US007557263B2

(12) United States Patent
Gruis et al.

(10) Patent No.: US 7,557,263 B2
(45) Date of Patent: Jul. 7, 2009

(54) METHODS OF INCREASING POLYPEPTIDE ACCUMULATION IN PLANTS

(75) Inventors: Darren B. Gruis, Des Moines, IA (US); Rudolf Jung, Des Moines, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 5 days.

(21) Appl. No.: 11/971,708

(22) Filed: Jan. 9, 2008

(65) Prior Publication Data

US 2008/0124804 A1 May 29, 2008

Related U.S. Application Data

(60) Division of application No. 11/016,055, filed on Dec. 17, 2004, which is a continuation of application No. 09/934,066, filed on Aug. 21, 2001, now Pat. No. 6,855,871.

(60) Provisional application No. 60/226,804, filed on Aug. 21, 2000.

(51) Int. Cl.
*C12N 15/82* (2006.01)
*C12N 15/87* (2006.01)
*C01H 21/20* (2006.01)
*A01H 5/00* (2006.01)

(52) U.S. Cl. .................. 800/285; 800/286; 800/287; 536/23.1; 536/23.6

(58) Field of Classification Search ........................ None
See application file for complete search history.

(56) References Cited

U.S. PATENT DOCUMENTS

| 5,723,763 | A | 3/1998 | Mariani et al. |
| 5,955,653 | A | 9/1999 | Scott et al. |
| 6,087,558 | A | 7/2000 | Howard et al. |
| 6,855,871 | B2 * | 2/2005 | Gruis et al. .................. 800/298 |

FOREIGN PATENT DOCUMENTS

WO    WO 95/07993    3/1995

OTHER PUBLICATIONS

Bowie, J.U., et al, "Deciphering the Message in Protein Sequences: Tolerance to Amino Acid Substitutions," *Science*, Mar. 16, 1990, pp. 1306-1310, vol. 247.
Bryant, J., "Anitsense RNA Makes Good Sense," *Trends in Biotechnology*, Feb. 1989, pp. 20-21, vol. 7, No. 2.
D'Hondt, K.D., et al., "An Aspartic Proteinase Present in Seeds Cleaves *Arabidopsis* 2 S Albumin Precursors in Vitro," *The Journal of Biological Chemistry*, Oct. 5, 1993, pp. 208884-20891, vol. 268, No. 28.
D'Hondt, K.D., et al., "Aspartic Proteinase Genes in the Brassicaceae *Arabidopsis thaliana* and *Brassica napus*," *Plant Molecular Biology* 1997, pp. 187-192, vol. 33.
Ellgaard, L., et al., "Setting the Standards: Quality Control in the Secretory Pathway," *Science*, Dec. 3, 1999, pp. 1882-1888, vol. 286.

Hara-Nishimura, I., and Nishimura, M., "Proglobulin Processing Enzyme in Vacuoles Isolated from Developing Pumpkin Cotyledons," *Plant Physiol.* 1987, pp. 440-445, vol. 85.
Hara-Nishimura, I., et al., "Molecular Characterization of a Vacuolar Processing Enzyme Related to a Putative Cysteine Proteinase of *Schistosoma mansoni*," *The Plant Cell*, Nov. 1993, pp. 1651-1659, vol. 5.
Hara-Nishimura, I., et al., "Vacuolar Processing Enzyme Responsible for Maturation of Seed Proteins," *J. Plant Physiol.*, 1995, pp. 632-640, vol. 145.
Herman, E.M., and Larkins, B.A., "Protein Storage Bodies and Vacuoles," *The Plant Cell*, Apr. 1999, pp. 601-613, vol. 11.
Hilder, V. A., et al., "A Novel Mechanism of Insect Resistance Engineered into Tobacco," *Nature*, 1987, pp. 160-163, vol. 300.
Hiraiwa, N., et al., "Vacuolar Processing Enzyme is Self-catalytically Activated by Sequential Removal of the C-terminal and N-terminal Propeptides," *FEBS Letters* 1999, pp. 213-216, vol. 447.
Jung, R.,et al., "Site-Specific Limited Proteolysis of Legumin Chloramphenicol Acetyl Transferase Fusions In Vitro and in Transgenic Tobacco Seeds," *Journal of Experimental Botany*, Jan. 1993, pp. 343-349, vol. 44, Supplement.
Jung, R., et al., "The Role of Proteolysis in the Processing and Assembly of 11S Seed Globulins," *The Plant Cell*, Mar. 1998, pp. 343.357, vol. 10.
Kinoshita, T., et al., "The Sequence and Expression of the γ-VPE Gene, One Member of a Family of Three Genes for Vacuolar Processing Enzymes in *Arabidopsis thaliana*," *Plant Cell Physiol.* 1995, pp. 1555-1562, vol. 36, No. 8.
Kinoshita, T., et al., "Vacuolar Processing Enzyme is Up-regulated in the Lytic Vacuoles of Vegetative Tissues during Senescence and Under Various Stressed Conditions," *The Plant Journal* 1999, pp. 43-53, vol. 19, No. 1.
Martienssen R.A., "Functional Genomics: Probing Plant Gene Function and Expression with Transposons," *Proc. Natl. Acad. Sci.*, Mar. 1998, pp. 2021-2026, vol. 95.
McConnell, J.R., et al., Role of PHABULOSA and PHAVOLUTA in Determining Radial Patterning in Shoots, *Nature*, Jun. 7, 2001, pp. 709-713, vol. 411.
Moonan, F., and Mirkov, T. E., "Analysis of Genotypic Diversity Among North, South, and Central American Isolates of Sugarcane Yellow Leaf Virus: Evidence for Colombian Origins and for Intraspecific Spatial Phylogenetic Variation," *Journal of Virology*, Feb. 2002, pp. 1339-1348, vol. 76, No. 3.

(Continued)

*Primary Examiner*—Stuart F. Baum
*Assistant Examiner*—Li Zheng
(74) *Attorney, Agent, or Firm*—Alston & Bird LLP

(57) ABSTRACT

The present invention provides methods and compositions directed to the production of polypeptides in plant protein storage tissue. Methods of the invention include methods for producing polypeptides in protein storage tissues by decreasing the level of protease activity in the plant protein storage tissue. Compositions of the invention include plants that are genetically modified such that the activity of one or more proteases is reduced or eliminated, transformed seeds obtained from these genetically modified plants, and sequences encoding a novel member of the VPE cysteine protease family found in seed, ε-VPE. These methods and compositions find utility in altering the nutritional or other qualities of seed, and in producing useful proteins including pharmacological or industrial proteins.

19 Claims, No Drawings

OTHER PUBLICATIONS

Muntz, K., et al, Synthesis, Processing, and Targeting of Legume Seed Proteins, *Proc Phytochem Soc Eur* 1993, pp. 128-146, vol. 35.

Muntz, K., "Deposition of Storage Proteins," *Plant Molecular Biology* 1998, pp. 77-99, vol. 38.

Nielsen, N.C., et al., "Synthesis and Assembly of 11S Globulins," *J. Plant Physiol.* 1995, pp. 641-647, vol. 145.

Saalbach, G., et al., "Stable Expression of Vicilin from *Vicia faba* with Either Additional Single Methionine Residues but Failure of Accumulation of Legumin with an Attached Peptide Segment in Tobacco Seeds," *Molecular Breeding* 1995, pp. 245-258, vol. 1.

Scott, M.P., et al., "A Protease Responsible for Post-translational Cleavage of a Conserved Asn-Gly Linkage in Glycinin, the Major Seed Storage Protein of Soybean," *Proc. Natl. Acad Sci. USA*, Jan. 1992, pp. 658-662, vol. 89.

Vitale, A. and Denecke, J., "The Endoplasmic Reticulum—Gateway of the Secretory Pathway," *The Plant Cell*, Apr. 1999, pp. 615-628, vol. 11.

Schaller 2004 Planta 220:183-197.

* cited by examiner

METHODS OF INCREASING POLYPEPTIDE ACCUMULATION IN PLANTS

CROSS-REFERENCE TO RELATED APPLICATIONS

This application is a divisional of U.S. Utility application Ser. No. 11/016,055, filed Dec. 17, 2004, which is a continuation of U.S. Utility application Ser. No. 09/934,066, filed Aug. 21, 2001, now U.S. Pat. No. 6,855,871, which claims the benefit of U.S. Provisional Application No. 60/226,804, filed Aug. 21, 2000, each of which is hereby incorporated in its entirety by reference herein.

REFERENCE TO A SEQUENCE LISTING SUBMITTED AS A TEXT FILE VIA EFS-WEB

The official copy of the sequence listing is submitted concurrently with the specification as a text file via EFS-Web, in compliance with the American Standard Code for Information Interchange (ASCII), with a file name of 3339032SequenceListing.txt, a creation date of Jan. 9, 2008, and a size of 12 KB. The sequence listing filed via EFS-Web is part of the specification and is hereby incorporated in its entirety by reference herein.

FIELD OF THE INVENTION

The present invention relates to genetic manipulations of protein processing, more particularly to the increased deposition of polypeptides in plants.

BACKGROUND OF THE INVENTION

Many plant storage tissues (seeds, leaves, roots, and tubers), accumulate sizable reserves of proteins during development. As an example, cultivated soybean seeds contain an average of about 40% protein, and in some varieties protein levels reach as much as 55% of the dry weight. The abundance of proteins in legume seeds has made them the primary dietary protein source and stimulated an interest in developing approaches to genetically engineer seeds to improve their nutritional quality. A related objective (as yet unrealized) is to utilize the protein synthesis and storage capacity of seed crops for the production of pharmacological or industrial proteins.

A major obstacle to improving the nutritional and functional qualities of plants has been the extremely low levels of accumulation of genetically modified or heterologous recombinant proteins that accumulate in plants transformed to express these proteins. For example, in experiments using comparable promoters, it has been shown that unmodified or very slightly altered seed storage proteins will accumulate in transgenic seed, but non-seed proteins or more highly modified seed storage proteins fail to accumulate (Hoffman et al. (1988) Plant Mol. Biol. 11:717-729; Jung et al. (1993) J. Exp. Bot. 44:343-349; Nielsen et al. (1995) J. Plant Physiol. 145:641-647; Saalbach et al. (1995) Mol. Breeding 1:245-258; Jung et al. (1998) Plant Cell 10:343-357). It has also been shown that antibodies fail to express in vacuoles (Frigerio et al (2000) Plant Physiol. 123:1483-1494) and that bovine β-casein fails to express in soybean seed vacuoles (Phillip et al. (2000) Annual Meeting for the American Society of Plant Physiology "Plant Biology 2000" Poster Abstract # 53, San Diego, Calif.)

Two of the most prevalent protein storage organs in plants are seed and paravienal mesophyll cells in leaves. Other plant storage tissues include tubers and roots. Storage proteins, especially those processed through the secretory pathway, generally undergo multiple post-translational processing steps including folding, assembly, intracellular sorting, and proteolytic processing, prior to final deposition (Müntz et al., (1993) Proc. Phytochem. Soc. Eur. 35:128-146; Muntz (1998) Plant Mol. Biol. 38:77-99; Herman and Larkins (1999) Plant Cell 11:601-613). The general mechanism of seed storage protein processing and deposition is highly conserved in dicot crop species including canola and soybean as well as monocot crop species including rice, wheat, and maize. Accumulation and deposition of the proteins is accomplished by compartmentalization in specialized vacuoles termed protein storage vacuoles and or protein bodies (Hara-Nishimura et al (1995) J. Plant Physiol. 145:632-640; Muntz (1998) Plant Molec. Biol. 38:77-99; Herman and Larkins (1999) Plant Cell 11:601-613).

The proteolytic processing steps of protein deposition in vacuoles include specific polypeptide cleavage steps accomplished by proteases localized to the storage vacuole (Bassham et al. (2000) Curr. Opin. Cell Biol. 12:491-495). Storage proteins that accumulate in vacuoles have therefore co-evolved with the environment of the storage vacuole such that only a select few protease sites exist or are accessible to these proteases (Hara-Nishimura et al. (1987) Plant Physiol. 85:440-445; D'Hondt et al., (1993) J. Biol. Chem. 268:10884-10891; Hara-Nishimura et al. (1993) Plant Cell 5:1651-1659; Hara-Nishimura et al. (1995) J. Plant Physiol. 145:632-640).

The proteases that have thus far been implicated in the proteolytic processing of storage protein are the vacuolar processing enzyme family of cysteine proteases (also referred to as legumains), and specific aspartic proteases (Hara-Nishimura et al. (1987) Plant Physiol 85:440-445; D'Hondt et al. (1993) J. Biol. Chem. 268:20884-20891; Hara-Nishimura et al. (1993) Plant Cell 5:1651-1659; Hara-Nishimura et al. (1995) J. Plant Physiol. 145:632-640; Kinoshita et al. (1995) Plant Cell Physiol. 36:1555-1562; D'Hondt et al. (1997) Plant Molec. Biol. 33:187-192; Barrett et al., ed. (1998) Handbook of Proteolytic Enzymes, Academic Press, San Diego, pp 746-749). In plants, vacuolar processing enzymes (VPE's) comprise a small gene family of plant asparaginyl endopeptidases implicated in the control of several important cellular process in addition to storage protein proteolysis. In Arabidopsis thaliana, three VPE's have been identified and are designated α-VPE, β-VPE, and γ-VPE. The genomic sequence of α-VPE is available as GenBank Accession No. AC004747 and the cDNA sequence at DDBJ Accession No. D61393; the genomic sequence of β-VPE is available as GenBank Accession No. AC007190 and the cDNA sequence at DDBJ Accession No. D61394; and the genomic sequence of γ-VPE is available as GenBank Accession No. ATF26P21 and the cDNA sequence at DDBJ Accession No. D61395. Two of these VPE's (α and γ) have been shown to be most abundant in vegetative tissue while the third (β-VPE) appears to be predominantly expressed in seed. The vegetative VPE's appear to be involved in protein turnover and mobilization of amino acid reserves in vegetative tissue during plant senescence process. β-VPE's localization and the results of in vitro processing suggest that β-VPE acts as the protease responsible for the cleavage and maturation of several major classes of seed storage proteins (Hara-Nishimura et al. (1991) FEBS Lett. 294:89-93).

Methods are needed to increase the accumulation of polypeptides of interest, both to enhance their quality and to harness the potential for the production of heterologous proteins in plant tissues.

SUMMARY OF THE INVENTION

The present invention provides methods and compositions directed to the production of polypeptides in plants. Methods of the invention include methods for producing polypeptides in plants and methods for altering the structural and functional properties of endogenous plant proteins by altering the activity of protein processing proteases. While protease activity may be decreased by any method, preferred embodiments include the reduction of the expression of specific protein processing proteases; the modification of the nucleotide sequence encoding the polypeptide of interest such that the polypeptide will no longer be cleaved by one or more protein processing proteases, or a combination of reduction of specific protein processing proteases and modification of the nucleotide sequence encoding the polypeptide such that the polypeptide will no longer be cleaved by one or more protein processing proteases.

Compositions of the invention include plants that are genetically modified such that the activity of one or more of the protein processing proteases is altered, or that express modified recombinant polypeptides that are not subject to proteolytic degradation by protein processing proteases; transformed seed and other protein storage organs obtained from these genetically modified plants; and sequences encoding ε-VPE, a novel member of the VPE cysteine protease family which is expressed in seed.

DETAILED DESCRIPTION OF THE INVENTION

One explanation offered for the failure to accumulate significant quantities of modified recombinant proteins in plant storage organs is that one or more of the proteolytic protein processing steps required for the stable deposition of seed is deleterious to the integrity of these proteins. An example of the failure to accumulate significant quantities of modified recombinant protein includes the processing of 11s globulin protein of soybean seed, in which conservative changes in the amino acid sequence of this protein resulted in spurious proteolysis of the protein when exposed to a protease preparation from the seed storage vacuole normally involved in specific proteolytic processing for further assembly and deposition of the protein in seed (Jung et al. (1993) *J. Exp. Bot.* 44:343-349; Nielsen et al. (1995) *J. Plant Physiol.* 145:641-647; Saalbach et al. (1995) *Mol. Breeding.* 1:245-258; Jung et al. (1998) *Plant Cell* 10:343-357). The object of the current invention is to provide methods and compositions for the stable expression and accumulation of polypeptides of interest in plants by reducing the activity of specific protein processing proteases of polypeptides that normally occurs in the protein storage organs of plants, by expressing recombinant polypeptides that have been modified such that they are no longer subject to proteolytic degradation by said proteases, or by a combination of the above methods. The results of such accumulation of polypeptides of interest can be but are not limited to the altered composition of plants for increased nutritional value, enhanced food processing properties, and production of precursor molecules for industrial or pharmaceutical use.

"Activity" of a polypeptide as used herein refers to the ability of a polypeptide to perform one or more biological functions attributed to the polypeptide in a biological context. A polypeptide's activity can be determined by any method available in the art. For example, the activity of a protease can be determined by assaying for the proteolytic cleavage of a substrate of the protease. "Wild type activity" in reference to a polypeptide as used herein refers to a polypeptide whose activity is similar to that most commonly seen for the polypeptide in a population that has not been genetically modified to alter the activity of the polypeptide.

"Polypeptide" refers to any monomeric or multimeric protein or peptide.

"Polypeptide of interest" as used herein refers to any polypeptide intended for expression in plant seed using the methods or compositions of the present invention. As non-limiting examples, pharmacological polypeptides (e.g., for veterinary or medical uses) or industrial polypeptides (e.g., enzymes or precursors) can be produced according to the present invention.

The terms "expression" and "production" refer to the biosynthesis of a gene product, including the transcription and translation of said gene product.

"Proteolytic degradation" in reference to a polypeptide of the invention refers to a process of proteolytic cleavage of the polypeptide that renders it inactive or otherwise incapable of carrying out its function.

The invention encompasses isolated or substantially purified nucleic acid or protein compositions. An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein having less than about 30%, 20%, 10%, 5%, (by dry weight) of contaminating protein. When the protein of the invention or biologically active portion thereof is recombinantly produced, preferably culture medium represents less than about 30%, 20%, 10%, or 5% (by dry weight) of chemical precursors or non-protein-of-interest chemicals.

Fragments and variants of the disclosed nucleotide sequences and polypeptides encoded thereby are also encompassed by the present invention. By "fragment" is intended a portion of the nucleotide sequence or a portion of the amino acid sequence and hence polypeptide encoded thereby. Fragments of a nucleotide sequence may encode protein fragments that retain the biological activity of the native protein and hence proteolyze plant protein storage proteins. Alternatively, fragments of a nucleotide sequence that are useful as hybridization probes generally do not retain biological activity. Thus, fragments of a nucleotide sequence may range from at least about 20 nucleotides, about 50 nucleotides, about 100 nucleotides, and up to the full-length nucleotide sequence encoding the polypeptides of the invention.

Increasing the Accumulation of Polypeptides of Interest by Reducing Protein Processing Protease Activity In the present invention, the accumulation of polypeptides of interest in plant storage organs can be reduced by decreasing or eliminating the activity of one or more protein processing proteases. For example, protein processing proteases in *Arabidopsis thaliana* include, but are not limited to α-VPE, β-VPE, γ-VPE (DDJB Accession Nos. D61393, D61394, and D61395, respectively; herein incorporated by reference), and δ-VPE (SEQ ID NO:2), the aspartic proteases AP1 (nucleotides 72142-74181 of GenBank Accession No. U51036, herein incorporated by reference) and AP2 (nucleotides 46660-49174 of GenBank Accession No. AF076243, herein incorporated by reference), papain-type thioproteases, subtilisin-type proteases, and other serine proteases. See D'Hondt et al. (1997) *Plant Mol. Biol.* 33:187-192, for a discussion of AP2.

Soybean has at least five VPE genes, two of which have a seed-preferred expression pattern. The activity of these proteases can be reduced or altered by any method available in the art, including but not limited to, insertional mutagenesis (i.e. TUSC, transposon tagging, T-DNA insertion), gene targeting (i.e. chimerplasty), sense suppression (co-suppression), antisense suppression, expression of specific protein processing protease inhibitors, or an increase in the level or activity of endogenous protease inhibitors. Alternatively, any combination of the above methods may be used to reduce or alter protease activity in plants. Transformed plants with reduced or altered protein processing protease activity can be selected by standard methods available in the art such as, for example, assaying for proteolytic activity, immunoblotting using antibodies which bind to specific protein processing proteases, assaying for the products of a reporter or marker gene, and the like.

Plants with reduced activity for a single protein processing protease can be used for the present invention. Alternatively, plants with reduced activity for more than one protein processing protease can be used. Those of ordinary skill in the art realize that this can be accomplished in any one of a number of ways. For example, each of the respective sense or antisense sequences for such enzymes can be operably linked to a promoter and then joined together in a single continuous fragment of DNA comprising an expression cassette. Such an expression cassette can be used to transform a plant to produce the desired outcome. Alternatively, separate plants can be transformed with expression cassettes containing one or a subset of the desired set of sense or antisense sequences and selected as described supra. A single plant with reduced activity for multiple protein processing proteases can then be produced by transforming a selected protein processing protease-deficient plant to reduce the activity of one or more additional protein processing proteases, and selecting for plants with multiple deficiencies in protein processing protease activity. Multiple rounds of transformation and selection may be required to produce the desired plant.

Alternatively, a single plant with reduced activity for multiple protein processing proteases can be produced through one or more rounds of cross pollination utilizing the previously selected seed-protease deficient plants as parents. Methods for cross pollinating plants are well known to those skilled in the art, and are generally accomplished by allowing the pollen of one plant, the pollen donor, to pollinate a flower of a second plant, the pollen recipient, and then allowing the fertilized eggs in the pollinated flower to mature into seeds. Progeny containing the entire complement of heterologous coding sequences of the two parental plants can be selected from all of the progeny by standard methods available in the art as described supra for selecting transformed plants. If necessary, the selected progeny can be used as either the pollen donor or pollen recipient in a subsequent cross pollination.

Accumulation of the polypeptide of interest in plant storage organs can be accomplished by transforming a plant with reduced or eliminated activity for one or more specific protein processing proteases described above with an expression cassette or DNA construct comprising a nucleotide sequence encoding the polypeptide of interest. Alternatively, accumulation of endogenous forms of polypeptides of interest will already occur in those plants for which the appropriate protein processing protease activities have been reduced or eliminated. Both approaches can be used in all plant species by modifying the homologs or orthologs of the described protein processing proteases Orthologs can be identified in syntenious genomic regions of other plant species.

This method may also be used to accumulate or alter protein in soybeans, which may also affect protein concentrates or isolates. Soy protein products are generally categorized into three major groups: soy flours and grits containing about 45 to 54% soy protein on a moisture free basis; soy protein concentrates containing 65 to 90% protein on a moisture free basis; and soy protein isolates having a minimum of 90% protein on a moisture free basis. Soy protein isolates are preferred in many applications because of their higher protein content, easier digestibility, and improved flavor as compared with soy flours, grits and concentrates. The invention pertains to the production of soy protein isolates, which are the most highly refined soy protein products commercially available.

Conventional processes for preparing most soy protein products, including soy isolates, usually include the steps of washing, cracking, dehulling, and defatting soybeans to produce defatted soy flakes. Soy protein isolates are produced by first extracting the protein from the defatted soybean flakes with water or mild alkali solution having a pH of about 7 to about 10. An alkaline extract containing the soy protein and soluble impurities is then separated from the insoluble fibrous residue. The resulting soluble fraction is acidified to a pH at about the isoelectric point of the soy protein, about pH 4.4-4.6, with a food-grade acid, typically hydrochloric acid, to precipitate the protein as a curd. The protein curd is then separated from the remaining liquid fraction containing soluble impurities (the whey), typically by centrifuging the curd and whey and separating the centrifuged curd from the whey.

Increasing the Accumulation of Recombinant Polypeptides in Plant Storage Organs by Modifying the Sequence Encoding the Recombinant Polypeptide In another method of the current invention, the aforementioned plants designed to contain reduced or eliminated activity for a protein processing protease is used in a method for determining whether this protease proteolyses a polypeptide of interest. An expression cassette comprising a nucleotide sequence encoding the polypeptide of interest is inserted into plants or plant cells with reduced or eliminated activity for a particular protein processing protease. Proteins are collected from protein storage organs using methods available in the art, and the existence of protease cleavage sites in the polypeptide of interest is determined by comparing the size or expression levels of the polypeptide of interest expressed in the wild type protein storage organ with that expressed in modified protein storage organs using any method available in the art. For example, such methods include but are not limited to one or two dimensional polyacrylamide gel electrophoresis coupled with immunoblotting using antibodies directed against the polypeptide of interest, amino-terminal protein sequencing, and mass spectroscopy. See, for example, Mastsudaira, P (ed.) (1993) *A Practical Guide to Protein and Peptide Purification for Microsequencing*, Academic Press, Inc. When a protein processing protease is shown to proteolyse a polypeptide of interest, the exact cleavage sites for the protease in the polypeptide can be ascertained by sequencing isolated fragments of the polypeptide of interest produced in the storage organ with wild type protease activity suing any method known in the art. See, for example, U.S. Pat. No.

6,064,754 to Parkeh et al., herein incorporated by reference. Other methods know in the art can also be used to characterize protease that act upon a specific polypeptide of interest, such as in vitro assays or computer analysis of sequence or structure.

Polypeptides of interest characterized as above can be produced and accumulated in plant storage organs by modifying the nucleotide sequence encoding the polypeptide of interest to remove the protease cleavage sites acted upon in vivo by specific protein processing proteases. Similar methods are also used to examine proteolysis of endogenous plant proteins acted upon by these specific protein processing proteases. This data is used to make predictions about the potential proteolytic processing sites contained in peptides of interest. Taken together, these methods provide for the rational modification of the nucleotide sequence encoding the polypeptide of interest, which is then modified to change the identity of one or more amino acids at the cleavage site such that the protease will no longer proteolyse the polypeptide of interest. Guidance as to appropriate amino acid substitutions that do not affect the activity of the polypeptide of interest may be found in the model of Dayhoff et al. (1978) *Atlas of Protein Sequence and Structure* (Natl. Biomed. Res. Found., Washington, D.C.), herein incorporated by reference. Those skilled in the art prefer to alter the nucleotide sequence such that it results in conservative amino acid substitutions, such as exchanging one amino acid with another having similar properties, and in the case of rational design to alter those predicted proteolytic sites with peptide bonds exposed to the surface of the polypeptide of interest.

Methods for modifying a nucleotide sequence to alter the amino acids encoded by the sequence are known in the art, See, for example, Kunkel (1985) *Proc. Natl. Acad. Sci. USA* 82:488-492; Kunkel et al. (1987) *Methods in Enzymol.* 154: 367-382; U.S. Pat. No. 4,873,192; Walker and Gaastra, eds. (1983) *Techniques in Molecular Biology* (MacMillan Publishing Company, New York) and the references cited therein. The modified nucleotide sequence encoding the polypeptide of interest that is no longer subject to proteolysis by protein processing proteases is incorporated into an expression cassette and inserted into a plant for production and accumulation in plant protein storage tissues.

Plants and transformed seeds with reduced protein processing protease activity are provided in the present invention. Also provided are plants and transformed seed from plants that have been transformed with a nucleotide sequence encoding a polypeptide of interest, where the nucleotide sequence has been modified to eliminate at least one protease cleavage site in the polypeptide of interest.

Any polypeptide of interest can be produced in the present invention. Polypeptides of interest encompassed by the invention include but are not limited to modified or unmodified plant polypeptides as well as those from other sources including eukaryotes, procaryotes, and non-naturally occurring polypeptides. Polypeptides of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of polypeptides of interest for expression will change accordingly.

One category of polypeptides of interest are those that affect agronomically important traits such as oil, starch, and protein content. Polypeptides of interest include those that increase the content of oleic acid, saturated and unsaturated oils, increase the levels of lysine and sulfur, provide essential amino acids, or modify starch content. Hordothionin protein modifications are described in U.S. Pat. Nos. 5,703,049, 5,885,801, 5,885,802, and 5,990,389, herein incorporated by reference. Another example is lysine and/or sulfur rich seed protein encoded by the soybean 2S albumin described in U.S. Pat. No. 5,850,016, and the chymotrypsin inhibitor from barley, described in Williamson et al. (1987) *Eur. J. Biochem.* 165:99-106, the disclosures of which are herein incorporated by reference.

Commercial traits can also be affected by expression of a polypeptide of interest that could increase for example, starch for ethanol production. Another important commercial use of transformed plants is the production of polymers and bioplastics such as described in U.S. Pat. No. 5,602,321. Similarly, the methods taught may be used to accumulate or alter protein in soybeans, which may also affect the resulting soy protein concentrates or isolates.

The current invention may be utilized for the production of pharmacological or industrial polypeptides of interest. Examples of pharmacological and industrial polypeptides include, but are not limited to: insulin, human growth hormone, pepsin, cellulases, pectinases, hemicellulases, phytases, hydrolases, esterases, peroxidases, fibrinogen, plasma proteins, serum albumin, factor IX, factor XIII, thrombin, protein C, xylanase, isoamylase, glucoamylase, α-amylase, lysozyme, catalase, β-glucanase, β-casein, lactase, urease, glucose isomerase, superoxide dismutase, pullulanase, invertase, streptavidin, avidin, alkaline phosphatase, aprotinin, β-glucuronidase, protease inhibitors, aprotinin, pepsin, chymotrypsin, trypsin, papain, kinases, phosphatases, antibodies, deoxyribonucleases, ribonucleases, phosphlipases, lipases, peptide hormones, and enzymes.

ε-VPE, a Novel Member of the VPE Family of Proteases

Sequences encoding a novel seed protease that is a member of the VPE cysteine protease family are also encompassed by the present invention. A nucleotide sequence for *Arabidopsis* ε-VPE is set forth in SEQ ID NO:1 and the amino acid sequence encoded by the *Arabidopsis* ε-VPE coding sequence (nucleotides 83-1440 of SEQ ID NO:1) is set forth in SEQ ID NO:2. SEQ ID NO:3 shows the *Arabidopsis* genomic sequence containing the ε-VPE coding sequence. This protease is primarily expressed in developing seed based on the number of clones found in a developing seed/carpel library (4 out of 13,437 clones) versus the number of clones found in flower, leaf, or seedling libraries (0 out of 23,443 clones). The *Arabidopsis* ε-VPE protein shares 58.5%, 55.2%, and 59.8% sequence similarity with *Arabidopsis* α-VPE, β-VPE, and γ-VPE, respectively, as determined by the GCG gap algorithm using a gap creation penalty of 12, a penalized length of 12, gap extension penalty of 4, and 10 as the number of randomizations. These percentages were calculated using the entire amino acid sequence, which includes signal peptides and carboxy and amino terminal pro sequences.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988) *CABIOS* 4:11-17; the local homology algorithm of Smith et al. (1981) *Adv. Appl. Math.* 2:482; the homology alignment algorithm of Needleman and Wunsch (1970) *J. Mol. Biol.* 48:443-453; the search-for-similarity-method of Pearson and Lipman (1988) *Proc. Natl. Acad. Sci.* 85:2444-2448; the algorithm of Karlin and Altschul (1990)

*Proc. Natl. Acad. Sci. USA* 872264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See the website at ncbi.nlm.nih.gov. Alignment may also be performed manually by inspection.

Unless otherwise stated, sequence identity/similarity values provided herein refer to the value obtained using GAP Version 10 using the following parameters: % identity using GAP Weight of 50 and Length Weight of 3; % similarity using Gap Weight of 12 and Length Weight of 4, or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

GAP uses the algorithm of Needleman and Wunsch (1970) *J. Mol. Biol.* 48: 443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff and Henikoff (1989) *Proc. Natl. Acad. Sci. USA* 89:10915).

A fragment of ε-VPE nucleotide sequence that encodes a biologically active portion of an ε-VPE protein of the invention will encode at least 15, 25, 30, 50, 100, 150, 200, 250, 300, 350, 400, or 450 contiguous amino acids, or up to the total number of amino acids present in a full-length ε-VPE protein of the invention (for example, 466 amino acids for SEQ ID NO:2). Fragments of an ε-VPE nucleotide sequence that are useful as hybridization probes or PCR primers generally need not encode a biologically active portion of an ε-VPE protein.

Thus, a fragment of an ε-VPE nucleotide sequence may encode a biologically active portion of an ε-VPE protein, or it may be a fragment that can be used as a hybridization probe or PCR primer using methods disclosed below. A biologically active portion of an ε-VPE protein can be prepared by isolating a portion of the ε-VPE nucleotide sequence of the invention, expressing the encoded portion of the ε-VPE protein (e.g., by recombinant expression in vitro), and assessing the activity of the encoded portion of the ε-VPE protein. Nucleic acid molecules that are fragments of an ε-VPE nucleotide sequence comprise at least 16, 20, 50, 75, 100, 150, 200, 250, 300, 350, 400, 450, 500, 550, 600, 650, 700, 800, 900, 1,000, 1,100, 1,200, 1,300, or 1,400, 1500 nucleotides, or up to the number of nucleotides present in a full-length ε-VPE nucleotide sequence disclosed herein (for example, 1595 nucleotides for SEQ ID NO:1).

By "variants" is intended substantially similar sequences. For nucleotide sequences, conservative variants include those sequences that, because of the degeneracy of the genetic code, encode the amino acid sequence of one of the proteases of the invention. Naturally occurring allelic variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis but which still encode a protease of the invention. Generally, variants of a particular nucleotide sequence of the invention will have at least 40%, 50%, 60%, 65%, 70%, generally at least about 75%, 80%, 85%, preferably at least about 90%, 91%, 92%, 93%, 94%, 95%, 96%, 97%, and more preferably at least about 98%, 99% or more sequence identity to that particular nucleotide sequence as determined by sequence alignment programs described elsewhere herein using default parameters.

By "variant" protein is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Variant proteins encompassed by the present invention are biologically active, that is they continue to possess the desired biological activity of the native protein, that is, protease activity as described herein. Such variants may result from, for example, genetic polymorphism or from human manipulation. Biologically active variants of a native protease of the invention will have at least 40%, 50%, 60%, 65%, 70%, generally at least 75%, 80%, 85%, preferably at least about 90%, 91%, 92%, 93%, 94%, 95%, 96%, 97%, and more preferably at least about 98%, 99% or more sequence identity to the amino acid sequence for the native protein as determined by sequence alignment programs described elsewhere herein using default parameters. A biologically active variant of a protein of the invention may differ from that protein by as few as 1-15 amino acid residues, as few as 1-10, such as 6-10, as few as 5, as few as 4, 3, 2, or even 1 amino acid residue.

The polypeptides of the invention may be altered in various ways including amino acid substitutions, deletions, truncations, and insertions. Methods for such manipulations are generally known in the art. For example, amino acid sequence variants of the protease can be prepared by mutations in the DNA. Methods for mutagenesis and nucleotide sequence alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the polypeptide of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be used.

Thus, the genes and nucleotide sequences of the invention include both the naturally occurring sequences as well as mutant forms. Likewise, the polypeptides of the invention encompass both naturally occurring proteins as well as variations and modified forms thereof. Such variants will continue to possess the desired protease activity. Obviously, the mutations that will be made in the DNA encoding the variant must not place the sequence out of reading frame and preferably will not create complementary regions that could produce secondary mRNA structure. See, EP Patent Application Publication No. 75,444.

The deletions, insertions, and substitutions of the polypeptide sequence encompassed herein are not expected to produce radical changes in the characteristics of the polypeptide. However, when it is difficult to predict the exact effect of the substitution, deletion, or insertion in advance of doing so, one skilled in the art will appreciate that the effect will be evaluated by routine screening assays. That is, the activity can be evaluated by assaying the cleavage of known substrates of the protease.

Variant nucleotide sequences and proteins also encompass sequences and proteins derived from a mutagenic and recombinogenic procedure such as DNA shuffling. With such a procedure, one or more different protease coding sequences can be manipulated to create a new protease possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the proteases of the invention and other known protease genes to obtain a new gene coding for a protein with an improved property of interest, such as an increased $K_m$. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The nucleotide sequences of the invention can be used to isolate corresponding sequences from other organisms, particularly other plants. In this manner, methods such as PCR, hybridization, and the like can be used to identify such sequences based on their sequence homology to the sequence set forth herein. Sequences isolated based on their sequence identity to the entire protease sequence described herein or to fragments thereof are encompassed by the present invention.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the protease sequences of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, an entire protease sequence disclosed herein, or one or more portions thereof, may be used as a probe capable of specifically hybridizing to corresponding protease sequences and messenger RNAs. To achieve specific hybridization under a variety of conditions, such probes include sequences that are unique among protease sequences and are preferably at least about 10 nucleotides in length, and most preferably at least about 20 nucleotides in length. Such probes may be used to amplify corresponding protease sequences from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringent conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m=81.5°$ C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

Thus, isolated sequences that encode for proteases and that hybridize under stringent conditions to the protease sequence disclosed herein, or to fragments thereof, are encompassed by the present invention.

Derivatives of the coding sequences can be made by site-directed mutagenesis to increase the level of preselected amino acids in the encoded polypeptide. For example, the gene encoding the barley high lysine polypeptide (BHL) is derived from barley chymotrypsin inhibitor, U.S. application Ser. No. 08/740,682, filed Nov. 1, 1996, now abandoned, and WO 98/20133, the disclosures of which are herein incorporated by reference. Other proteins include methionine-rich plant proteins such as from sunflower seed (Lilley et al. (1989) *Proceedings of the World Congress on Vegetable Protein Utilization in Human Foods and Animal Feedstuffs*, ed. Applewhite (American Oil Chemists Society, Champaign, Ill.), pp. 497-502; herein incorporated by reference); corn (Pedersen et al. (1986) *J. Biol. Chem.* 261:6279; Kirihara et al. (1988) *Gene* 71:359; both of which are herein incorporated by reference); and rice (Musumura et al. (1989) *Plant Mol. Biol.* 12:123, herein incorporated by reference). Other agronomically important genes encode latex, Floury 2, growth factors, seed storage factors, and transcription factors.

It is recognized that with these nucleotide sequences, antisense constructions, complementary to at least a portion of the messenger RNA (mRNA) for the protease sequences can be constructed. Antisense constructions for other proteases may also be constructed, either by using sequences known in the art, or by isolating nucleotide sequences encoding proteases using methods known in the art. Antisense nucleotides are constructed to hybridize with the corresponding mRNA. Modifications of the antisense sequences may be made as long as the sequences hybridize to and interfere with expression of the corresponding mRNA. In this manner, antisense constructs having 70%, preferably 80%, more preferably 85% sequence identity to the corresponding antisensed sequences may be used. Furthermore, portions of the antisense nucleotides may be used to disrupt the expression of the target gene. Generally, sequences of at least 50 nucleotides, 100 nucleotides, 200 nucleotides, or greater may be used.

The nucleotide sequences of the present invention, or nucleotide sequences encoding any protease, may also be used in the sense orientation to suppress the expression of endogenous genes in plants in a process sometimes termed sense suppression or co-suppression. Methods for suppressing gene expression in plants using nucleotide sequences in the sense orientation are known in the art. The methods generally involve transforming plants with a DNA construct comprising a promoter that drives expression in a plant operably linked to at least a portion of a nucleotide sequence that corresponds to the transcript of the endogenous gene. Typically, such a nucleotide sequence has substantial sequence identity to the sequence of the transcript of the endogenous gene, preferably greater than about 65% sequence identity, more preferably greater than about 85% sequence identity, most preferably greater than about 95% sequence identity. See, U.S. Pat. Nos. 5,283,184 and 5,034,323; herein incorporated by reference.

The sequences encoding the polypeptides of interest of the invention, as well as the sense suppression and antisense suppression nucleotide sequences, are provided in expression cassettes for expression in the plant of interest. For production of a polypeptide of interest of the invention, the cassette will include 5' and 3' regulatory sequences operably linked to a sequence encoding the polypeptide of interest. For sense or antisense suppression of a plant gene, the cassette will included at least a promoter that drives expression in a plant operably linked to the sense or antisense nucleotide sequence described supra. By "operably linked" is intended a functional linkage between a promoter and a second sequence wherein the promoter sequence initiates and mediates transcription of the DNA sequence corresponding to the second sequence. Generally, operably linked means that the nucleic acid sequences being linked are contiguous and, where necessary to join two polypeptide coding regions, contiguous and in the same reading frame. The cassette may additionally contain at least one additional gene to be cotransformed into the organism. Alternatively, the additional gene(s) can be provided on multiple expression cassettes.

Such an expression cassette is provided with a plurality of restriction sites for insertion of the sequence encoding the polypeptide of interest to be under the transcriptional regulation of the regulatory regions. The expression cassette may additionally contain selectable marker genes.

For production of a polypeptide of interest of the invention, the expression cassette will include in the 5'-3' direction of transcription, a transcriptional and translational initiation region, a sequence encoding the polypeptide of interest, and a transcriptional and translational termination region functional in plants. The transcriptional initiation region, the promoter, may be native or analogous or foreign or heterologous to the plant host. Additionally, the promoter may be the natural sequence or alternatively a synthetic sequence. By "foreign" is intended that the transcriptional initiation region is not found in the native plant into which the transcriptional initiation region is introduced.

While it may be preferable to express the sequences using heterologous promoters, the native promoter sequences may be used. Such constructs would change expression levels of the polypeptide of interest in the plant. Thus, the phenotype of the plant would be altered.

The termination region may be native with the transcriptional initiation region, may be native with the operably linked DNA sequence of interest, or may be derived from another source. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the gene(s) may be optimized for increased expression in the transformed plant. That is, the genes can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165(2):233-238), MDMV leader (Maize Dwarf Mosaic Virus) (*Virology* 154:9-20), and human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81:382-385). See also, Della-Cioppa et al. (1987) *Plant Physiol.* 84:965-968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

The nucleic acids can be combined with constitutive, tissue-preferred, or other promoters for expression in plants. Constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; and 5,608,142.

Tissue-preferred promoters can be utilized to target enhanced expression of the polypeptide of interest within a particular plant tissue. Tissue-preferred promoters include Yamamoto et al. (1997) *Plant J.* 12(2)255-265; Kawamata et al. (1997) *Plant Cell Physiol.* 38(7):792-803; Hansen et al. (1997) *Mol. Gen. Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol. Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression Leaf-specific promoters are known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20): 9586-9590.

Root-preferred promoters are known and can be selected from the many available from the literature or isolated de novo from various compatible species. See, for example, Hire et al. (1992) *Plant Mol. Biol.* 20(2): 207-218 (soybean root-specific glutamine synthetase gene); Keller and Baumgartner (1991) *Plant Cell* 3(10):1051-1061 (root-specific control element in the GRP 1.8 gene of French bean); Sanger et al. (1990) *Plant Mol. Biol.* 14(3):433-443 (root-specific promoter of the mannopine synthase (MAS) gene of *Agrobacterium tumefaciens*); and Miao et al. (1991) *Plant Cell* 3(1):11-22 (full-length cDNA clone encoding cytosolic glutamine synthetase (GS), which is expressed in roots and root nodules of soybean). See also Bogusz et al. (1990) *Plant Cell* 2(7): 633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed rolC and rolD root-inducing genes of *Agrobacterium rhizogenes* (see *Plant Science* (Limerick) 79(1):69-76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see EMBO J. 8(2):343-350). The TR1' gene, fused to nptII (neomycin phosphotransferase II) showed similar characteristics. Additional root-preferred promoters include the VfENOD-GRP3 gene promoter (Kuster et al. (1995) Plant Mol. Biol. 29(4):759-772); and rolB promoter (Capana et al. (1994) *Plant Mol. Biol.* 25(4):681-691. See also U.S. Pat. Nos. 5,837,876; 5,750,386; 5,633,363; 5,459,252; 5,401,836; 5,110,732; and 5,023,179.

"Seed-preferred" promoters include both "seed-specific" promoters (those promoters active during seed development such as promoters of seed storage proteins) as well as "seed-germinating" promoters (those promoters active during seed germination). See Thompson et al. (1989) *BioEssays* 10:108, herein incorporated by reference. Such seed-preferred promoters include, but are not limited to, Cim1 (cytokinin-induced message); cZ19B1 (maize 19 kDa zein); milps (myo-inositol-1-phosphate synthase); and celA (cellulose synthase) (see the copending application entitled "Seed-Preferred Promoters," U.S. application Ser. No. 09/377,648, filed Aug. 19, 1999, now U.S. Pat. No. 6,225,529, herein incorporated by reference). Gama-zein is a preferred endosperm-specific promoter. Glob-1 is a preferred embryo-specific promoter. For dicots, seed-specific promoters include, but are not limited to, bean β-phaseolin, napin, β-conglycinin (see, for example, Kitamura et al. (1984) *Theor. Appl. Genet.* 68:253-257, Cho et al. (1989) *Nucleic Acids Res.* 17:4386-4389, Kim et al. (1990) *Agric. Biol. Chem.* 54:1543-1550, Kim et al. (1990) *Protein Engineering* 3:725-731, Jung et al. (1998) *Plant Cell* 10:343-357, and Katsube et al. (1998) *BBA Gen. Subjects* 1379:107-117, herein incorporated by reference), soybean lectin, cruciferin, and the like. For monocots, seed-specific promoters include, but are not limited to, maize 15 kDa zein, 22 kDa zein, 27 kDa zein, g-zein, waxy, shrunken 1, shrunken 2, globulin 1, etc.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). See generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Aci. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference.

The above list of selectable marker genes is not meant to be limiting. Any selectable marker gene can be used in the present invention.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (Townsend et al., U.S. Pat. No. 5,563,055; Zhao et al., U.S. Pat. No. 5,981,840), direct gene transfer (Paszkowski et al. (1984) *EMBO J.* 3:2717-2722), and ballistic particle acceleration (see, for example, Sanford et al., U.S. Pat. No. 4,945,050; Tomes et al., U.S. Pat. No. 5,879,918; Tomes et al., U.S. Pat. No. 5,886, 244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); and McCabe et al. (1988) *Biotechnology* 6:923-926). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440-444 (maize); Fromm et al. (1990) *Biotechnology* 8:833-839 (maize); Hooykaas-Van Slogteren et al. (1984) *Nature (London)* 311:763-764; Bowen et al., U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, New York), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved.

The present invention may be used for transformation of any plant species, including, but not limited to, monocots and dicots. Examples of plants of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum. Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Preferably, plants of the present invention are crop plants (for example, corn, alfalfa, sunflower, *Brassica*, soybean, cotton, safflower, peanut, sorghum, wheat, millet, tobacco, etc.), more preferably corn and soybean plants, yet more preferably corn plants.

EXPERIMENTAL

Materials

The *Arabidopsis* library constructed with multiple independent defective suppressor-mutator transposon insertions is described in Tissier et al. (1999) *Plant Cell* 11:1841-52, herein incorporated by reference.

Isolation of an *Arabidopsis* Plant with a Suppressor-Mutator Transposon Inserted in the β-VPE Gene.

A putative transposon insertional event was detected in one pool of 50 parent plants of the *Arabidopsis* library described above by determining that DNA isolated from this pool contained a transposon adjacent sequence corresponding to β-VPE. The pool was obtained from Jonathon Jones of the Sainsbury Laboratory in Norwich, United Kingdom.

Approximately 600 seedlings from this pool were grown and genomic DNA isolated from subpools of 25 plants. Polymerase chain reaction suing sequence-specific primers from the transposon sequence and the β-VPE sequence were used to detect which subpools contained genomic DNA containing the β-VPE transposon insertional event by virtue that such an insertion in β-VPE would allow for the amplification of a β-VPE specific fragment. One subpool was found to have such an amplified fragment and DNA was prepared separately from each plant within this subpool. The same assay was repeated on these individual plants and two plants were isolated as containing a copy of genomic DNA with a transposon within β-VPE. The exact transposon insertion site was determined by using PCR fragments produced from the aforementioned reactions. These DNA fragments were subcloned into the TOPO TA cloning vector and sequence on an automated sequencing machine utilizing M13 Forward and M13 Reverse primers, which hybridize to the vector sequence adjacent to the insert. The transposon was found to be residing within the coding sequence of β-VPE.

Characterization of the β-VPE Knockout Plant.

Plants homozygous for the transposon insertional event were isolated utilizing PCR with primers specific to the β-VPE genomic DNA flanking the insertion site. Homozygous plants were determined as those containing DNA which was incapable of amplifying a β-VPE genomic DNA flanking the insertion site. Homozygous plants were determined as those containing DNA which was incapable of amplifying a β-VPE fragment corresponding in size to the expected product produced by these gene specific primers while still amplifying a specific fragment utilizing a transposon specific primer and gene specific primer. Messenger RNA from 50-70 mature seed from homozygous β-VPE plants and wildtype plants was isolated using the mRNA DIRECT™ brand RNA isolation kit, and first strand cDNA from this RNA was produced using the SUPERSCRIPT™ II brand first strand cDNA synthesis kit (Life Technologies). 2 μl of a total of 10 μl resulting from these isolations is subjected to PCR utilizing gene-specific primers at the 3' end of the gene designed such that amplification of genomic DNA can be differentiated from amplification of cDNA by virtue of the presence of an intron in the genomic DNA that alters the size of the amplified product. cDNA was isolated from mature seed of wildtype and β-VPE knockout plants and analyzed in this fashion. The lack of amplified product from β-VPE plants compared to wildtype was confirmation that the transposon insertion in β-VPE did prevent any detectable amount of mature β-VPE message from being made in these plants. Seed from these homozygous plants was collected and 50-70 seed were ground and then boiled for 5 minutes in the presence of 50 μl protein extraction buffer solubilize total protein contained in these seeds. Insoluble debris and oil bodies were removed by three sequential centrifugation and extraction steps in a microcentrifuge. 10-20 μl of this extract was then combined with SDS-PAGE sample buffer and electrophoresed on 4-20% Tris-glycine mini-gels (BioRad). This SDS-PAGE analysis, coupled with protein immunoblots and protein microsequencing has demonstrated that compared to normal unaltered plants, seed storage composition of the β-VPE knockout plants has changed. Protein immunoblots and protein microsequencing have shown detectable amounts of novel forms of the cruciferin and albumin class of proteins in plants devoid of β-VPE activity. To more completely characterize proteins altered in proteolytic processing by virtue of the lack of β-VPE activity, two-dimensional gel electrophoresis followed by mass-spectroscopy is performed on protein isolated from mature seed of β-VPE plants and wildtype plants. Proteins showing more than a 2-fold change in quantity are subjected to mass spectroscopy, followed by analysis using the Sequest software package and the public *Arabidopsis* genomic sequence database. This analysis allows determination of which proteins are processed. Exact identification of these proteins, coupled with data regarding sequence, pI, and molecular mass, allows for the identification of the processing sites of endogenous *Arabidopsis* seed proteins acted upon by β-VPE in vivo.

Identification of a Novel VPE Family Member ε-VPE.

A novel member of the VPE cysteine protease family, termed ε-VPE was identified from the DuPont *Arabidopsis* database, and the cDNA was sequenced in its entirety. A nucleotide sequence encoding *Arabidopsis* ε-VPE is set forth in SEQ ID NO:1 and the encoded *Arabidopsis* ε-VPE amino acid sequence is set forth in SEQ ID: 2. This protease is primarily expressed in developing seed based on the number of clones found in a developing seed/carpel library (4 out of 13,437 clones) versus the number of clones found in flower, leaf, or seedling libraries (0 out of 23,443 clones).

Isolation of an *Arabidopsis* plant with an Enhancer/Suppressor-Mutator Element Inserted in the ε-VPE Gene SLAT blots generated from the *Arabidopsis* library were obtained from the Sainsbury Laboratory. These blots area a tool for displaying all of the genomic DNA adjacent to transposon insertions within the above-described library. Probes for identifying ε-VPE fragments on this display blot were generated by PCR amplifying the genomic region of *Arabidopsis* DNA containing the coding region of the gene. This DNA was then used as a template to produce a digoxigenin (DIG) labeled ε-VPE probe. The SLAT blot was hybridized with this probe, washed, and developed according to the DIG labeling kit manufacturer's instructions (Roche). Two pools were identified in this fashion as containing plants which had ε-VPE DNA adjacent to a transposon insertion. Combined DNA from plants in each pool was obtained from the Sainsbury Laboratory and examined by the PCR using gene-specific and transposon-specific primers. The fragments generated by the PCR were sequence to characterize the exact insertion site of the transposon into the ε-VPE gene. Seed from each pool was planted and plants containing the transposon-tagged ε-VPE gene were isolated in a similar fashion to that described for β-VPE above.

Characterization of the ε-VPE Knockout Plant.

Plants homozygous for the ε-VPE insertional events are characterized in the same fashion as described for β-VPE above.

*Arabidopsis* Plants with Knockouts of Both β-VPE and ε-VPE

Plants homozygous for a ε-VPE transposon disruption and plants homozygous for a β-VPE transposon disruption were crossed and the seed from these crosses selected. The seed was grown out, DNA isolated, and the PCR using allele-specific primers was used to confirm that these plants each contained both an ε-VPE::dSpm allele and a VPE::dSpm allele. These plants were allowed to self pollinate and progeny was again grown out. DNA is isolated from these plants and the PCR performed to determine which of the segregating progeny is homozygous for both insertional events. These plants are allowed to self propagate and provide a line for which tow proteases are now removed.

Increased Accumulation of Vacuolar-Targeted Polypeptides of Interest in the Seed of *Arabidopsis* Deficient for Both β-VPE and ε-VPE.

An expression cassette containing a functional fusion of the soybean alpha prime beta-conglycinin promoter (for seed-preferred expression), the coding sequence of the sporamin signal peptide (for import into the secretory pathway), and the coding sequence of the sporamin propeptide (containing vacuolar targeting information) is linked in frame with the bovine sequence encoding B-casein milk protein, and further is connected with the nopaline synthase 3' untranslated region (UTR) as a terminator. Any other transgenic polypeptide of interest (for example green fluorescent protein, spider silk, bovine serum albumin, and so forth) is used in an alternative embodiment. Similarly, an alternative embodiment may use another signal peptide (for instance the lectin signal peptide, the alpha prime beta-conglycinin signal peptide, the signal peptide of a pathogene-related protein from tobacco, and so forth), other peptides with vacuole targeting information (for instance the barley lectin C-terminal propeptide, the C-terminal propeptide of the 2S albumin from Brazil nut, the N-terminal propeptide of tobacco chitinase, and so forth) and the beta-phaseolin promoter, the PsI lectin promoter or another promoter with expression in the seed and at the desired level. Yet another embodiment may use other 3'UTR sequences like the soybean alpha-prime beta-conglycinin 3' UTR or the 3' UTR of the beta-phaseolin gene. In a different embodiment, the beta-casein is fused to the signal peptide without a vacuolar targeting pro-peptide and is transported by a pathway that directs assembled polypeptides to the vacuole. This expression cassette is cloned into a T-DNA vector also designed to express the NPTII selectable marker gene and transformed into wild type *Arabidopsis* by vacuum infiltration of flowers. Selected transformants are crossed to *Arabidopsis* mutant lines that are either deficient in β-VPE or ε-VPE protease activity or both protease activities. Progeny plants of the crosses are self-pollinated and plants of the next generation are screened for events that are hemizygous or homozygous for the dominant beta casein transgene and are homozygous for the recessive insertion mutant alleles of the β-VPE and ε-VPE genes. These allele tests are conducted by PCR with gene and transposon specific primers. In a different embodiment, β-casein gene transgenic lines are crossed to transgenic *Arabidopsis* lines in which the β-VPE and ε-VPE genes are silenced by sense or antisense suppression. *Arabidopsis* plants expressing the β-casein gene alone or in combination with a deficiency in β-VPE and ε-VPE activity are analyzed for the accumulation of B-casein in mature seed. The stable accumulation of β-casein in mature seed of *Arabidopsis* deficient for β-VPE, ε-VPE or both β-VPE and ε-VPE, is two fold or more greater than that found in wildtype *Arabidopsis*. In an alternative embodiment, the transgenic polypeptide of interest is expressed in the vacuole of other plant tissue, such as the leaf, tuber or roots, with an appropriate promoter used for expression in such tissue. β-casein is used as a representative example of any protein of interest, the stable expression of which may be improved through the use of the present invention.

Expression of Transgenic Protein in a Dicot Cell Such as *Arabidopsis* or Soybean Various embodiments of this invention involve the expression of one or more transgenes in a dicot cell, such as an *Arabidopsis* cell or a soybean cell. Expression of a transgene in a dicot cell is well known in the art, and one method of accomplishing this in soybean is described below.

A seed-specific expression cassette composed of the promoter and transcription terminator from the gene encoding the β subunit of the seed storage protein phaseolin from the bean *Phaseolus vulgaris* (Doyle et al. (1986) J. Biol. Chem. 261:9228-9238) can be used for expression of the instant polypeptides in transformed soybean. The phaseolin cassette includes about 1650 nucleotides upstream (5') from the translation initiation codon and about 500 nucleotides downstream (3') from the translation stop codon of phaseolin. Between the 5' and 3' regions are the unique restriction endonuclease sites Nco I (which includes the ATG translation initiation codon), SmaI, KpnI and XbaI. The entire cassette is flanked by Hind III sites.

The cDNA fragment of this gene may be generated by polymerase chain reaction (PCR) amplification of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3-5 mm in length dissected from surface sterilized, immature seeds of the soybean cultivar A2872, can be cultured in the light or dark at 26° C. on an appropriate agar medium for 6-10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 ml liquid media on a rotary shaker, 150 rpm, at 26° C. with florescent lights on a 16:8 hour day/night schedule. Cultures are subcultured every two weeks by inoculating approximately 35 mg of tissue into 35 ml of liquid medium.

Soybean embryogenic suspension cultures may then be transformed by the method of particle gun bombardment (Klein et al. (1987) Nature (London) 327:70-73, U.S. Pat. No. 4,945,050). A DuPont Biolistic PDS1000/HE instrument (helium retrofit) can be used for these transformations.

A selectable marker gene which can be used to facilitate soybean transformation is a transgene composed of the 35S promoter from Cauliflower Mosaic Virus (Odell et al. (1985) Nature 313:810-812), the hygromycin phosphotransferase gene from plasmid pJR225 (from *E. coli*; Gritz et al. (1983) Gene 25:179-188) and the 3' region of the nopaline synthase gene from the T-DNA of the Ti plasmid of *Agrobacterium tumefaciens*. The seed expression cassette comprising the phaseolin 5' region, the fragment encoding the polypeptide of interest and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μl spermidine (0.1 M), and 50 μL CaCl$_2$ (2.5 M). The particle preparation is then agitated for three minutes, spun in a microfuge for 10 seconds, and the supernatant removed. The DNA-coated particles are then washed once in 400 μL 70% ethanol and resuspended in 40 μL of anhydrous ethanol. The DNA/particle suspension can be sonicated three times for one second each. Five μl of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Reduction of a Seed-Preferred Ortholog of βVPE in Soybean/Soybean Embryo Transformation A BLAST search of soybean EST libraries (DuPont database) with the sequences of the *Arabidopsis* VPEs yielded five contigs and five singletons comprising the VPE gene family in soybean. Library distribution data (electronic northern) clearly demonstrates that one of the three contigs encompasses a VPE preferentially expressed in developing pods and embryos of soybean seed and is most similar in expression pattern and sequence to β-VPE in *Arabidopsis*. The longest EST is sequenced and subcloned into an sense suppression construct. Soybean embryos are bombarded with a plasmid containing the β-VPE sense suppression insert operably linked to a soybean lectin promoter as described above Enhancement of Functional Properties of Soybean Protein Isolates from Protease Knockout Soybeans Compared to Wildtype The functional properties of a soybean protein isolate is altered or the amount of soybean protein isolate increased by utilizing protease knock out soybeans or soybeans with altered protease proteolytic processing. In another embodiment, the functional properties of a soybean protein isolate is altered or the amount of soybean protein isolate is increased by altering the sequence of the soybean protein isolate so that it is not acted upon, or is acted upon differently, by an endogenous protease. The soybean protein isolate may be altered in molecular weight, protein structure or isoelectric point.

In one embodiment, water retention properties of soybean protein isolates is altered. Water retention of soybean protein isolates is at least partially dependent on the proteolyzed state of the proteins in the isolate. This is demonstrated in a report describing the function of hydrolysis in decreasing the water binding capabilities of soy protein isolate for food processing purposes (Mietsch et al. (1989) *Nahrung* 33:9-15) To decrease the proteolyzed state of the major protein components of soybean seed β-VPE ortholog activity is greatly reduced as described above. Mature wildtype soybean protein isolates are compared to protein isolates generated from soybeans devoid of the β-VPE ortholog for the ability to bind water in a weight to volume relationship. In an alternate embodiment, the amount of soybean protein isolate is increased by altering the sequence of the soybean protein isolate so that it is not acted upon, or is acted upon differently, by a β-VPE ortholog in soybean.

Determination of Protease Sites of Single Chain Antibody Expressed in *Arabidopsis* Deficient in β-VPE, ε-VPE, AP1, AP2, and/or AP3

A single chain antibody is produced in an in vitro transcription/translation reaction and treated with vacuolar extracts from developing *Arabidopsis* seed 12-15 DAP. These extracts will be from either wild type *Arabidopsis* or *Arabidopsis* deficient in the aforementioned processing protease activities. Following treatment of the in vitro transcription/translation products with either one or the other vacuolar extracts described the resulting polypeptide products are compared utilizing 2-D gels and polypeptide fragments unique to the reaction using wild type vacuolar extracts analyzed by mass spectroscopy. Sequence of these fragments will provide a peptide map of the antibody allowing for accurate determination of polypeptide bonds cleaved by the processing proteases.

Modification of Single Chain Antibody for Increased Accumulation in Arabidopsis.

The protein processing sites of the single chain antibody determined in the prior section are modified as described and the modified single chain antibody gene expressed in *Arabidopsis* seed using previously described methods to a 2 fold higher accumulated level than prior to determination and modification of the protease cleavage sites.

Determination of Protease Sites of Single Chain Antibody Expressed in Soybean Deficient in Soybean Orthologs of β-VPE, ε-VPE, AP1, AP2, AP3

A single chain antibody is produced in an in vitro transcription/translation reaction and treated with vacuolar extracts from developing soybean seed 12-15 DAP. These extracts will be from either wild type soybean or soybean deficient in the aforementioned processing protease activities. Following treatment of the in vitro transcription/translation products with either one or the other vacuolar extracts described the resulting polypeptide products are compared utilizing 2-D gels and polypeptide fragments unique to the reaction using wild type vacuolar extracts analyzed by mass spectroscopy. Sequence of these fragments will provide a peptide map of the antibody allowing for accurate determination of polypeptide bonds cleaved by the processing proteases.

Modification of Single Chain Antibody for Increased Accumulation in Soybean.

The protein processing sites of the single chain antibody determined in the prior section are modified as described and the modified single chain antibody gene expressed in soybean seed using previously described methods to a 2 fold higher accumulated level than prior to determination and modification of the protease cleavage sites.

Applicability to Other Tissues

Although the teachings herein emphasize the invention expressed in seeds, the invention relates to proteins deposited in storage tissues, which are present in all cells. Thus, alternate embodiments consist of the invention express in tissue such as leaves, roots and tubers. In one embodiment, a transgenic protein (e.g. human antibody) is expressed in the storage vacuoles of tobacco leaf cells. As described above, the invention may be used to determine protease activity on the transgenic protein. The transgenic protein may be expressed by either altering the protein so that it is not acted upon by the protease or by altering the protease so that it is not expressed, or if expressed, does not substantially affect the transgenic protein.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method for increasing the accumulation of one or more polypeptides in a plant protein storage tissue, comprising genetically modifying a plant to reduce or eliminate the activity of at least one protease in a protein storage tissue, wherein said protease is selected from the group consisting of α-vacuolar processing enzyme, β-vacuolar processing enzyme, γ-vacuolar processing enzyme, ϵ-vacuolar processing enzyme, aspartic protease AP1, and aspartic protease AP2, and wherein said genetic modification is selected from the group consisting of insertional mutagenesis, antisense suppression and sense suppression of a nucleotide sequence that encodes the at least one protease.

2. The method of claim 1, wherein said protein storage tissue is seed tissue.

3. The method of claim 1, wherein said protein storage tissue is selected from the group consisting of tuber tissue, root tissue and leaf tissue.

4. The method of claim 1, wherein said protease comprises the amino acid sequence set forth in SEQ ID NO:2.

5. The method of claim 1, wherein said plant is a dicot.

6. The method of claim 5, wherein said dicot is selected from the group consisting of *Arabidopsis*, soybean, sunflower, canola, cotton, and safflower.

7. The method of claim 1, wherein said plant is a monocot.

8. The method of claim 7, wherein said monocot is selected from the group consisting of maize, wheat, rice, barley, oats, rye, and millet.

9. The method of claim 1, further comprising transforming said plant with an expression cassette comprising a promoter operably linked with a nucleotide sequence encoding a polypeptide of interest, wherein said promoter is selected from the group consisting of a constitutive promoter, a tissue-preferred promoter, a leaf-specific promoter, a root-preferred promoter, and a seed-preferred promoter.

10. The method of claim 1, wherein said protease is α-vacuolar processing enzyme.

11. The method of claim 1, wherein said protease is β-vacuolar processing enzyme.

12. The method of claim 1, wherein said protease is γ-vacuolar processing enzyme.

13. The method of claim 1, wherein said protease is ϵ-vacuolar processing enzyme.

14. The method of claim 1, wherein said protease is aspartic protease AP1.

15. The method of claim 1, wherein said protease is aspartic protease AP2.

16. The method of claim 1, wherein said plant is genetically modified to reduce or eliminate the activity of at least two proteases in said protein storage tissue.

17. The method of claim 16, wherein said protein storage tissue is seed tissue.

18. The method of claim 1, wherein said plant is genetically modified to reduce or eliminate the activity of at least three proteases in said protein storage tissue.

19. The method of claim 18, wherein said protein storage tissue is seed tissue.

* * * * *

SEQUENCE LISTING

<160> NUMBER OF SEQ ID NOS: 3

<210> SEQ ID NO 1
<211> LENGTH: 1560
<212> TYPE: DNA
<213> ORGANISM: Arabidopsis thaliana

<400> SEQUENCE: 1

| ctcacaagaa tcagattcaa gatagaagtt tttcaaacaa tgtctagtcc tcttggtcac | 60 |
| tttcagattc ttgtttttct tcatgctttg cttatcttct cagctgagtc ccgcaaaacc | 120 |
| caattgctga acgataatga tgttgaatct agcgacaaga gtgcaaaagg cacacgatgg | 180 |
| gctgttttag ttgctggatc aaatgaatat ataactaca ggcatcaggc tgacatatgc | 240 |
| cacgcgtatc agatactccg aaaaggcggt ttaaaagatg aaaacatcat tgtgtttatg | 300 |
| tatgatgata tcgcgttttc ctcggagaat cctaggcctg gagttatcat taataaacca | 360 |
| gatggagaag atgtttataa aggagttcct aaggactaca ctaaagaagc tgttaatgtt | 420 |
| caaaacttct acaatgtgtt acttggaaat gaaagtggcg tcacaggagg aaatggcaaa | 480 |
| gttgtgaaaa gtggtcctaa tgataatatc ttcatctatt atgctgacca tggagctcct | 540 |
| ggcttaatag cgatgcccac tggtgatgaa gttatggcaa agatttcaa tgaagtcttg | 600 |
| gagaagatgc ataagagaaa aaaatacaac aagatggtga tctatgttga agcatgtgaa | 660 |
| tcaggaagta tgtttgaagg gatttttaaag aaaaatctca acatatacgc agtgactgct | 720 |
| gctaattcta aagagagcag ctggggagtt tactgtcctg agtcatatcc tcctcctcct | 780 |
| tctgagattg gaacttgtct cggcgataca tttagcatct cttggcttga ggacagtgac | 840 |
| cttcatgaca tgagcaaaga gactttggag caacaatacc acgttgtaaa gagaagagta | 900 |
| ggatctgatg taccagagac ttctcatgta tgccgtttcg gaacagagaa gatgcttaaa | 960 |
| gattatcttt cctcttacat tggaagaaat cctgaaaacg ataacttcac tttcacggaa | 1020 |
| tccttttcct caccaatctc taattctggc ttggtcaatc cgcgcgatat tcctctgcta | 1080 |
| tacctccaga gaaagattca aaaagctcca atgggatcac ttgaaagcaa agaagctcag | 1140 |
| aagaaattgc ttgacgaaaa gaatcatagg aaacaaatcg atcagagcat tacagacatt | 1200 |
| ctgcggcttt cagttaaaca aaccaatgtc ttaaatctct taacttccac aagaacaaca | 1260 |
| ggacagcctc ttgtagacga ttgggattgc ttcaagactc tagttaatag cttcaagaat | 1320 |
| cactgcggtg caacggtgca ttacggattg aagtatacag gagcgcttgc caatatctgc | 1380 |
| aatatgggag tggatgtgaa gcaaactgtt tcagccattg aacaagcttg ttcgatgtaa | 1440 |
| tgatttgcaa aacaatgtga tattcgactt taaaaatatc aaagttaatt tcaataaaac | 1500 |
| tcgatgtaga gatggttggt tcatgatact acttttacat gaaaaaaaaa aaaaaaaaa | 1560 |

<210> SEQ ID NO 2
<211> LENGTH: 466
<212> TYPE: PRT
<213> ORGANISM: Arabidopsis thaliana

<400> SEQUENCE: 2

Met Ser Ser Pro Leu Gly His Phe Gln Ile Leu Val Phe Leu His Ala
1               5                   10                  15

Leu Leu Ile Phe Ser Ala Glu Ser Arg Lys Thr Gln Leu Leu Asn Asp
            20                  25                  30

Asn Asp Val Glu Ser Ser Asp Lys Ser Ala Lys Gly Thr Arg Trp Ala

-continued

```
             35                   40                  45
Val Leu Val Ala Gly Ser Asn Glu Tyr Tyr Asn Tyr Arg His Gln Ala
 50                  55                  60

Asp Ile Cys His Ala Tyr Gln Ile Leu Arg Lys Gly Gly Leu Lys Asp
 65                  70                  75                  80

Glu Asn Ile Ile Val Phe Met Tyr Asp Asp Ile Ala Phe Ser Ser Glu
 85                  90                  95

Asn Pro Arg Pro Gly Val Ile Ile Asn Lys Pro Asp Gly Glu Asp Val
100                 105                 110

Tyr Lys Gly Val Pro Lys Asp Tyr Thr Lys Glu Ala Val Asn Val Gln
115                 120                 125

Asn Phe Tyr Asn Val Leu Leu Gly Asn Glu Ser Gly Val Thr Gly Gly
130                 135                 140

Asn Gly Lys Val Val Lys Ser Gly Pro Asn Asp Asn Ile Phe Ile Tyr
145                 150                 155                 160

Tyr Ala Asp His Gly Ala Pro Gly Leu Ile Ala Met Pro Thr Gly Asp
165                 170                 175

Glu Val Met Ala Lys Asp Phe Asn Glu Val Leu Glu Lys Met His Lys
180                 185                 190

Arg Lys Lys Tyr Asn Lys Met Val Ile Tyr Val Glu Ala Cys Glu Ser
195                 200                 205

Gly Ser Met Phe Glu Gly Ile Leu Lys Lys Asn Leu Asn Ile Tyr Ala
210                 215                 220

Val Thr Ala Ala Asn Ser Lys Glu Ser Ser Trp Gly Val Tyr Cys Pro
225                 230                 235                 240

Glu Ser Tyr Pro Pro Pro Ser Glu Ile Gly Thr Cys Leu Gly Asp
245                 250                 255

Thr Phe Ser Ile Ser Trp Leu Glu Asp Ser Asp Leu His Asp Met Ser
260                 265                 270

Lys Glu Thr Leu Glu Gln Gln Tyr His Val Lys Arg Arg Val Gly
275                 280                 285

Ser Asp Val Pro Glu Thr Ser His Val Cys Arg Phe Gly Thr Glu Lys
290                 295                 300

Met Leu Lys Asp Tyr Leu Ser Ser Tyr Ile Gly Arg Asn Pro Glu Asn
305                 310                 315                 320

Asp Asn Phe Thr Phe Thr Glu Ser Phe Ser Ser Pro Ile Ser Asn Ser
325                 330                 335

Gly Leu Val Asn Pro Arg Asp Ile Pro Leu Leu Tyr Leu Gln Arg Lys
340                 345                 350

Ile Gln Lys Ala Pro Met Gly Ser Leu Glu Ser Lys Glu Ala Gln Lys
355                 360                 365

Lys Leu Leu Asp Glu Lys Asn His Arg Lys Gln Ile Asp Gln Ser Ile
370                 375                 380

Thr Asp Ile Leu Arg Leu Ser Val Lys Gln Thr Asn Val Leu Asn Leu
385                 390                 395                 400

Leu Thr Ser Thr Arg Thr Thr Gly Gln Pro Leu Val Asp Asp Trp Asp
405                 410                 415

Cys Phe Lys Thr Leu Val Asn Ser Phe Lys Asn His Cys Gly Ala Thr
420                 425                 430

Val His Tyr Gly Leu Lys Tyr Thr Gly Ala Leu Ala Asn Ile Cys Asn
435                 440                 445

Met Gly Val Asp Val Lys Gln Thr Val Ser Ala Ile Glu Gln Ala Cys
450                 455                 460
```

Ser Met
465

<210> SEQ ID NO 3
<211> LENGTH: 4320
<212> TYPE: DNA
<213> ORGANISM: Arabidopsis thaliana

<400> SEQUENCE: 3

| | | | | | |
|---|---|---|---|---|---|
| cagtgccacg | tgtcatcaac | cgctgggact | ttctgttaca | ttgaccctga | gtaccaacaa | 60 |
| actggaatgc | taggtgtgaa | atctgatgtc | tactcttttg | gtatcttgct | tctcgaactg | 120 |
| ctcacagcga | aaaggccgac | gggtttggct | tataccgttg | agcaagcaat | ggagcaaggg | 180 |
| aaattcaagg | atatgttaga | cccagcagtg | cctaactggc | cggtggaaga | agctatgtct | 240 |
| ttggcaaaga | ttgctcttaa | atgtgcacag | ctgagaagga | aagaccgacc | agacctcgga | 300 |
| aaagaggttt | taccagagct | caataaattg | agagctcgtg | cagatacgaa | tatgaatgg | 360 |
| atgatgttca | acttaagtag | aggtcgtcta | acaccaaatc | atagccaagt | gtccttgcca | 420 |
| ccagttgtaa | gtaatgaaaa | agctcttttgc | aattctagtc | tttaagttaa | aatctttgaa | 480 |
| atgctttggt | tgcaggatga | actaagtgta | tgctcggata | agtcttatac | acattcaagc | 540 |
| actgtatccg | acacagagaa | gaactcaggt | gcattagaga | accatatttt | ttccatcttc | 600 |
| tttaacattt | ttacaatgtg | tttgatccat | caaatcttac | agtttactct | gtttcttttc | 660 |
| cagaccaaaa | cgaagaggat | tagcatattt | tgtgtgttga | aggaaatgga | gtgagaccat | 720 |
| tgttaaagct | tatgtaattg | tgaatattgt | tgtatgtatg | tatgtatata | attcgtaaag | 780 |
| gaagaaaata | actgaaggaa | aaagttgagt | aggtttgtta | taatatctct | gcaaagacgc | 840 |
| aaactctttt | tttgatatgt | aagacaaaat | atatagacca | cataattcgc | accctaattc | 900 |
| taagaaactt | ctaaattgag | aaattggttc | atcgatttca | gtggaaagtg | gtacttagct | 960 |
| aaattgagaa | aggtgcctca | atttcagtag | aacctgacgc | aaaatttcgc | gatcatgcat | 1020 |
| gactcaaatt | ggtttattca | cttaaataaa | aaagttgttt | ccctatctag | ttgaagttct | 1080 |
| caattcaaac | gcaacttctt | acttttttctt | tttatttata | ctggaatgaa | ttttttcgtca | 1140 |
| atgctagacc | tcaatatttg | gtgattaagt | ccaaaaaatt | atagcaatat | tcattagtta | 1200 |
| aatcataata | atatttgtta | tttctgctaa | atatattagt | tttaaattgg | taaatatatc | 1260 |
| agtcatcata | ctttatatat | gtgcacaaga | aaaagaggaa | aaaaaactaa | cttttaataa | 1320 |
| attgaacgct | atcctctata | tctcgtcctg | gtccaaatgt | aaacttcaat | atccttttga | 1380 |
| ttttattgct | gattgcttta | aaaaatttca | caaacacttt | tatcattctt | ttattccacc | 1440 |
| aaaatctaca | gacataatac | tttgtaattt | tatgtaaaaa | tcttcaaaat | ttgggaaaag | 1500 |
| aaaaatcatt | taaatcaat | ttgcattaac | tggatttatt | tccaaaggtg | tggtattgtg | 1560 |
| tttatatatg | tggagttgtt | ggctagtaat | ataataagga | aaagagtgaa | acatatgtag | 1620 |
| tataacgtat | ttctagtttt | tttctctgta | ttaatgaatc | actaattaag | tagtatgcat | 1680 |
| taattgaatt | atcagaagct | ggtcacaaaa | gtctaccaaa | aaaacaaaa | aaattggtca | 1740 |
| gaagaaaatg | aaaataatga | gaataaaaaa | gggaaaaaaa | ataagaagct | agcaaacaaa | 1800 |
| gcaattaaca | tttcaaggca | gttaattcat | catgcaaggt | gcttatgtgt | gacaacgtca | 1860 |
| tgcgttactt | tttgcgtcta | cactcatctc | tctaacgcaa | tccactaatt | ctggtaatgg | 1920 |
| attctgctat | ttagaccagc | cagtttcttc | gtctctcaat | catcatccaa | aaacattctt | 1980 |
| ctcacaagaa | tcagattcaa | gatagaagtt | tttcaaacaa | tgtctagtcc | tcttggtcac | 2040 |

-continued

```
tttcagattc ttgttttct tcatgctttg cttatcttct cagctgagtc ccgcaaaacc    2100
caattgctga acgataatga tgttgaatct agcgacaaga gtgcaaaagg cacacgatgg    2160
gctgttttag ttgctggatc aaatgaatat tataactaca ggcatcaggt tgttaaatta    2220
tgtttgaacg tttaacataa caaaaaaaaa aaaggtccaa gcgagatttg tatgaactaa    2280
atcgaccgac gttttatttc acaggctgac atatgccacg cgtatcagat actccgaaaa    2340
ggcggtttaa aagatgaaaa catcattgtg tttatgtatg atgatatcgc gttttcctcg    2400
gagaatccta ggcctggagt tatcattaat aaaccagatg gagaagatgt ttataaagga    2460
gttcctaagg ttcttatttc tacttctttt gtgcgttatt tctacgttga attcaattac    2520
atatatatat tcaagttttg ttgttattgg ttgggtagga ctacactaaa gaagctgtta    2580
atgttcaaaa cttctacaat gtgttacttg gaaatgaaag tggcgtcaca ggaggaaatg    2640
gcaaagttgt gaaaagtggt cctaatgata atatcttcat ctattatgct gaccatggag    2700
ctcctggctt aataggtttt cttaatttta tgaaattatt acgtaccatc aatccatatc    2760
tataataaaa gattttctct tgatactacg aaaccgcgat tttctcagcg atgcccactg    2820
gtgatgaagt tatggcaaaa gatttcaatg aagtcttgga gaagatgcat aagagaaaaa    2880
aatacaacaa gatggtatat aactcaacca ttcgttacct agctttatac atatgtgttc    2940
tgtttttgaa tctctatggt gtgttttttt ggatgtttag gtgatctatg ttgaagcatg    3000
tgaatcagga agtatgtttg aagggatttt aaagaaaaat ctcaacatat acgcagtgac    3060
tgctgctaat tctaaagaga gcagctgggg agtttactgt cctgagtcat atcctcctcc    3120
tccttctgag attggaactt gtctcggcga tacatttagc atctcttggc ttgaggacag    3180
gtactgcaaa caaaaaagat tcaatcctta tggactattc gaatgatttg atttgttctt    3240
gaagaatatt tgttcatttg ttctatgttt tgtgtgtgtt tggggacagt gaccttcatg    3300
acatgagcaa agagactttg gagcaacaat accacgttgt aaagagaaga gtaggatctg    3360
atgtaccaga gacttctcat gtatgccgtt tcggaacaga gaagatgctt aaagattatc    3420
tttcctctta cattggaaga aatcctgaaa acgataactt cactttcacg gaatcctttt    3480
cctcaccaat ctctaattct ggcttggtca atccgcgcga tattcctctg ctatacctcc    3540
agagaaaggt gagctttttt cgggtttttt gatcatttta aacgaaagag ttttcagcat    3600
gttttaatgt ttattcatct cttagattca aaaagctcca atgggatcac ttgaaagcaa    3660
agaagctcag aagaaattgc ttgacgaaaa gaatcatagg aaacaaatcg atcagagcat    3720
tacagacatt ctgcggcttt cagttaaaca aaccaatgtc ttaaatctct taacttccac    3780
aagaacaaca ggacagcctc ttgtagacga ttgggattgc ttcaagactc tagtaacaaa    3840
ccacatctca aaccttgtta cttgtgttct acgcaacaac cattgcatta ttactaaacc    3900
agtgtatatc gaatgaaaat cgcaggttaa tagcttcaag aatcactgcg gtgcaacggt    3960
gcattacgga ttgaagtata caggagcgct tgccaatatc tgcaatatgg gagtggatgt    4020
gaagcaaact gtttcagcca ttgaacaagc ttgttcgatg taatgatttg caaaacaatg    4080
tgatattcga ctttaaaaat atcaaagtta atttcaataa aactcgatgt agagatggtt    4140
ggttcatgat actactttta catgaaaagc ttttaatcg atgataacgc gaaagtcttg    4200
gtctaaattt gtgaattgga ttcatggaac aataacctcg taccaactgt acggtacgga    4260
cggctgtact ttggttgagt tacccaataa tagtcttctt ccaataactt gttgaccacg    4320
```